United States Patent
Sewell (10) Patent No.: US 6,381,555 B1
(45) Date of Patent: Apr. 30, 2002

(54) MEASUREMENT SYSTEM

(75) Inventor: Roger Fane Sewell, Newnham (GB)

(73) Assignee: Cambridge Consultants Limited, Cambridge (GB)

( * ) Notice: Subject to any disclaimer, the term of this patent is extended or adjusted under 35 U.S.C. 154(b) by 0 days.

(21) Appl. No.: 09/601,339

(22) PCT Filed: Feb. 17, 1999

(86) PCT No.: PCT/GB99/00488

§ 371 Date: Oct. 16, 2000

§ 102(e) Date: Oct. 16, 2000

(87) PCT Pub. No.: WO99/41662

PCT Pub. Date: Aug. 19, 1999

(30) Foreign Application Priority Data

Feb. 17, 1998 (GB) .............................................. 9803368

(51) Int. Cl.⁷ .......................... G06F 10/14; G01N 15/00
(52) U.S. Cl. ........................ 702/181; 702/29; 702/128; 356/335
(58) Field of Search ................................ 702/127, 128, 702/181, 182, 26, 29, 44–45, 49–50; 356/335–339, 318; 250/564, 573–574; 703/2, 6

(56) References Cited

U.S. PATENT DOCUMENTS

| | | | | |
|---|---|---|---|---|
| 4,318,180 A | * | 3/1982 | Lundgvist et al. ............. | 702/29 |
| 4,661,913 A | * | 4/1987 | Wu et al. ...................... | 702/19 |
| 5,855,011 A | * | 12/1998 | Tatsuoka ....................... | 706/45 |
| 5,880,835 A | * | 3/1999 | Yamazaki et al. ........... | 356/336 |
| 6,076,083 A | * | 6/2000 | Baker ........................... | 706/45 |

* cited by examiner

*Primary Examiner*—Bryan Bui
(74) *Attorney, Agent, or Firm*—Oblon, Spivak, McClelland, Maier & Neustadt, P.C.

(57) ABSTRACT

The invention concerns measurement apparatus for obtaining measurements relating to an attributes or attributes θ of a succession of events in which an event generates a measurable physical reaction, the apparatus comprising generating device for generating a value D representing the physical reaction caused by an event, and inferential processing device for deriving the marginal distributions of a probability distribution for the attribute or attributes θ of the events by carrying out a Bayesian inferential process utilizing the value D, the marginal values of a prior probability distribution and a stored set of values representing a range of probability distributions for the occurrence of each of the events being measured, the inferential process being an iterative process in which the marginals posterior to one event are generated by updating the marginals prior to that event.

13 Claims, 7 Drawing Sheets

MEASUREMENT SYSTEM

FIELD OF THE INVENTION

The present invention concerns a method and apparatus for deriving information from physical events.

BACKGROUND AND SUMMARY OF THE INVENTION

There are many events from which it is desirable to have measurements but which are not susceptible to direct measurement or in which measurement of individual events can only be carried out with very great difficulty. A particularly important class of such events is the flow of particles in a stream of gaseous or liquid fluid. Systems of such particle flow include smoke in columns of air, unwanted particles in liquid systems such as high pressure hydraulic systems, and biological particles which can indicate the presence of bacteria or disease in urine. Measurement of all of these systems provides substantial problems in that the size of particles can vary, the velocity with which the particles are travelling can vary and the number of particles in any one unit of volume can also vary. Additionally the times of arrival of individual particles into the confines of the measurement apparatus cannot be predicted exactly and the shape and physical nature of the particles can vary. All these factors perturb the final measurement.

Nevertheless the detection and measurement of particles in flowing systems is frequently of great importance. One of the examples already given relates to the measurement of bacteria in urine. Accurate measurement of the size of such bacteria particles can give very good indications as to the presence or not of certain diseases. In high pressure hydraulic fluids involving filtering the breakdown of filters can cause catastrophic results and the measurement of particles in the hydraulic flow can provide an early indication as to the efficiency of the filter system.

As a result of these demands for measurement systems a number of particular sizing techniques have been developed. Some of these are based on Doppler methods and require the interferometric combination of crossed laser beams to create a structured pattern. This requires coherent laser light sources and precision lasers, or more recently the use of defraction gratings. The extent of the structured light field necessarily occupies a large part of the inspection volume and consequently requires quality optical components. An example of such a technique is disclosed in U.S. Pat. No. 4,854,705.

An example of a heuristic approach in which a more direct attempt is made to measure the individual sizes and velocities of particles in a flowing stream is described in International Patent Application No. WO93/16368. In this specification a flow of particles is passed through a cell and a structured monochromatic light field is projected into the cell. The particles pass transversely and successively through the spaced variations of the light field, the spacings of which are set in accordance with the expected range of particle size. Variations in light intensity caused by the passage of the particles relative to the light field are detected and the size of a particle can be calculated by plotting the mean peak signal of the sensor as a function of the normalised peak-to-trough variation in the output pulses generated by the passages of the particle through the light field. Such a system can be made in an extremely compact and relatively inexpensive manner but is not suitable for relatively large flow sizes where there are likely to be a substantial number of particles in the volume where the measurements are being made. Thus this system is not suited, for example, measuring the distribution of particles in the situation where it is required to provide measurements of smoke particles in a gas flow.

Thus the present invention is concerned with providing a solution to the above problems and in particular a solution to the problem of providing accurate measurements of multiple physical events which are not directly observable.

U.S. Pat. No. 5,347,541 discloses Bayesian blind equalizer for use in digital communication comprising a plurality of parallel processors. Each processor in turn generates an estimated signal and an updated metric in order to be able to decode digital data despite intersymbol interference.

UK Patent specification No GB-2209414-A discloses a navigation system using a recursive estimator employing Bayesian logic.

International Patent Specification No. WO92/03905 discloses a method and apparatus for optimally allocating resources and discloses an iterative process utilising a probabilistic network in which each node corresponds to a variable and each arc corresponds to a constraint so that the topology of the network directly reflects the structure of the problem. The network is iterated until it reaches a stable state.

U.S. Pat. No. 4,661,913 discloses a flow apparatus through which unknown particles to be measured are passed, data generated by the passage of the particles stored, and this date is then compared with data detected from sample particles in order to clarify the unknown particles.

BRIEF DESCRIPTION OF THE DRAWINGS

In order that the present invention may be more readily understood an embodiment thereof will now be described by way of example and with reference to the accompanying drawings, in which.

DETAILED DESCRIPTION OF THE INVENTION

When considering the passage of an unknown particle through a light field it will be appreciated that the passage of the particle can have two main effects which can be detected by means of appropriate sensors. Firstly, the particle can obscure, that is it directly interfere with the passage of the light, or secondly it can scatter the light. The detection of these effects is an indication of the presence of the particle but is in itself a poor indication of the size, velocity and shape of the particle. Factors which cannot be directly deduced from the detected light include the size of the particle r, its coordinates within the measurement area z,y, its velocity v, its shape el, and the exact time of its arrival $T_o$.

In most measurement systems and in particular in the embodiment being described, the main unknown of interest is particle size.

It will be appreciated that a direct measurement of size of a particle such as a particle of smoke or grit in a flow of oil is not practicable in a rapid, real-time manner. That is the event which is to be measured is to some extent unobservable. The present embodiment accordingly proposes a system which is based on the probability of the size of a particle causing a detected event. It will accordingly be appreciated that the following description is concerned with the processing of detected data so as to arrive at probabilities rather than direct measurements.

Figure 1:
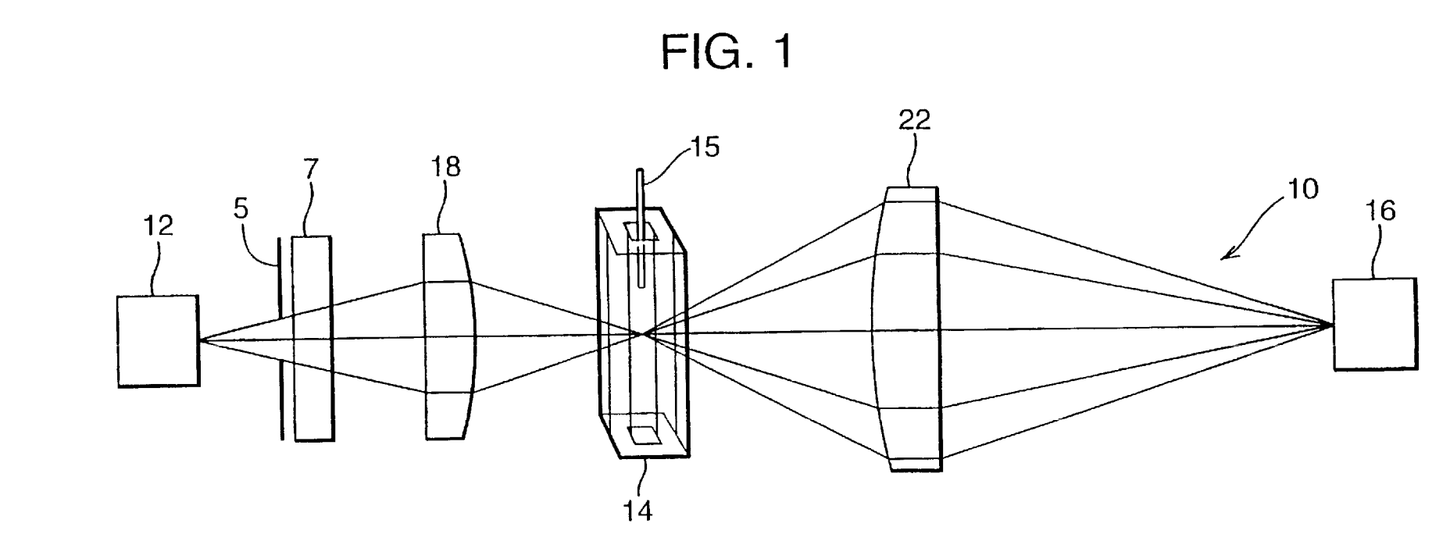
FIG. 1 is a cross-section through an embodiment of a particle measurement system.

Referring now to FIG. 1 of the accompanying drawings, this shows in diagrammatic form the optical layout of apparatus for sizing particles in a fluid stream. The apparatus is generally indicated at 10 and comprises a light source 12, a flow cell 14 through which a fluid flows at 15 and a light detector 16.

The light source 12 will be described in greater details hereinafter and is imaged by lenses indicated at 18 into the inspection volume of the flow cell 14. The light source 12 provides a series of spaced intensity peaks in the inspection volume transverse to the flow of particles to be measured through the inspection volume. In the present embodiment the light source provides three focused facets and the orientation of the long side of these facets is normal to the flow direction. The magnification of the light source is chosen so that the separation (q) of the image bars of the lines approximate to the range of particle size to be measured.

Light from the image volume in the flow cell is collected by lens 22 into the detector 16. The detector 16 can be a PIN diode or an avalanche photodiode.

Figure 2:
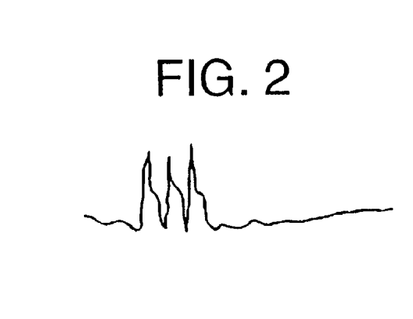
FIG. 2 illustrates a sample reading.

Particles that traverse the focused light field are thus exposed to light from each facet or focused variation in light intensity in turn. The intensity of light detected is thus modulated with a frequency U/q, where U is a particle transverse velocity and with intensity given by the convolution of the particle scattering cross-section with the structured light image. A particle P of diameter D where D>>q effectively smears out the structure. Particles for which D<q partially resolve the structure and thus partially modulate the signal intensity and particles for which modulate the signal intensity and particles for which D<<q fully resolve the structure and display full modulation with intensity limited only by the detection noise limit. A typical output for a particle passing through the structured light field is shown in the graph of FIG. 2.

It will be appreciated as already stated that the signals detected by the sensor can never be an exact representation of particle size. Amongst other factors the shape and nature of the particle will also affect its impact on the light as will its co-ordinates of passage relative to the focal plane.

It is a general concern of the present invention to establish these probabilities with such a degree of certainty that they can be taken as actual measurements for practical purposes.

Figure 3:
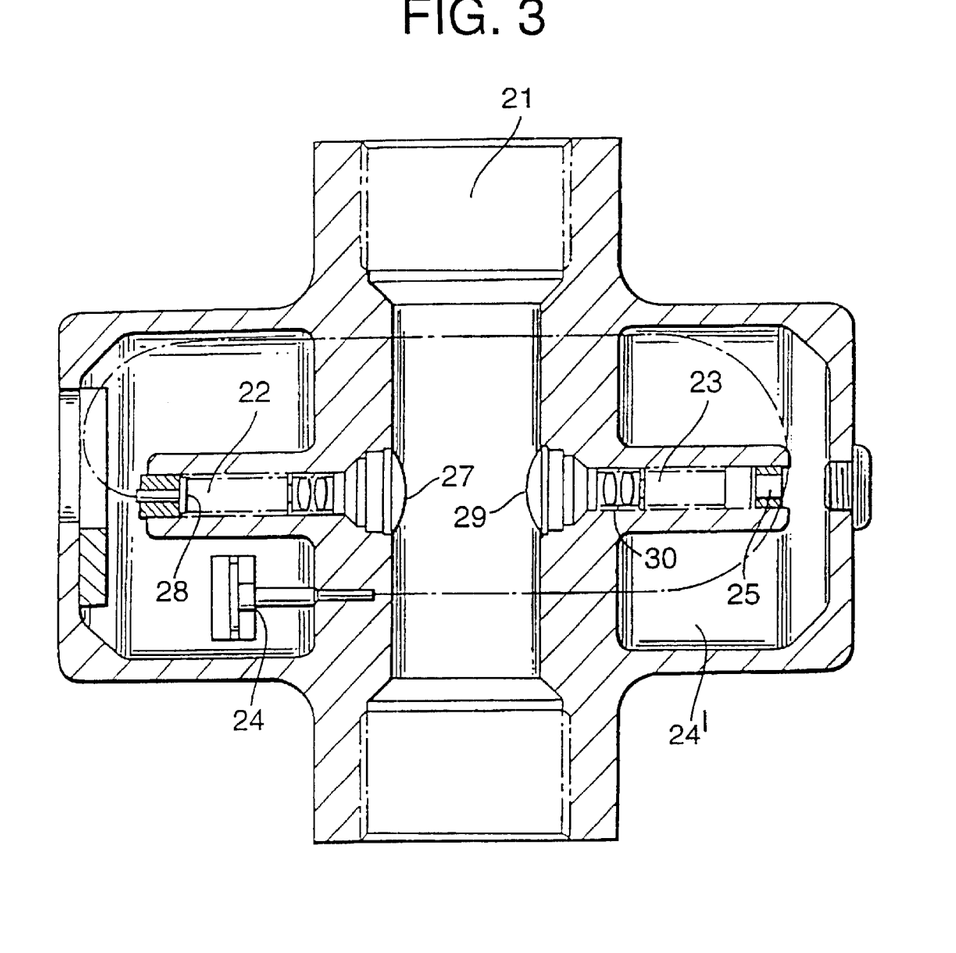
FIG. 3 is a sectional plan view of an embodiment of a measurement device.
Figure 3A:
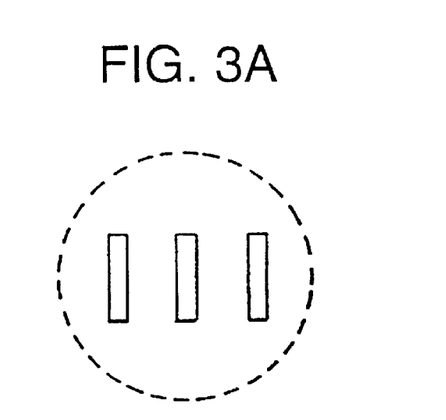

Referring now to FIG. 3 of the accompanying drawings, this shows a particular version of the flow cell, light source and light detector shown in diagrammatic form in FIG. 1. Thus the apparatus in FIG. 3 comprises a pipe 21 through which liquid or gas can flow. Chambers 22 and 23 extend from diametrically opposed sides of pipe 21 and respectively house a light source in the form of LED 24 and a photodetector 25. Lenses 26 correspond to the lens 18 of FIG. 1. In order to avoid problems caused by changing refractive indices in the fluid flowing through the pipe 21, the light is projected into the measurement volume via a curved window 27. Structure is given to the light intensities in the measurement volume by means of a three bar grating 28 located in front of end of an optical fibre 24' coupled to LED 24 and shown in plan in FIG. 3A. It is of course possible that the structured light could be generated by an appropriately facetted LED. The light exiting the measurement volume passes via a curved window 29 similar to window 27 via a lens system 30 to the receiving light sensor 25, whereupon the output of the light sensor is taken to the control circuit shown in FIG. 4 of the accompanying drawings.

Figure 4:
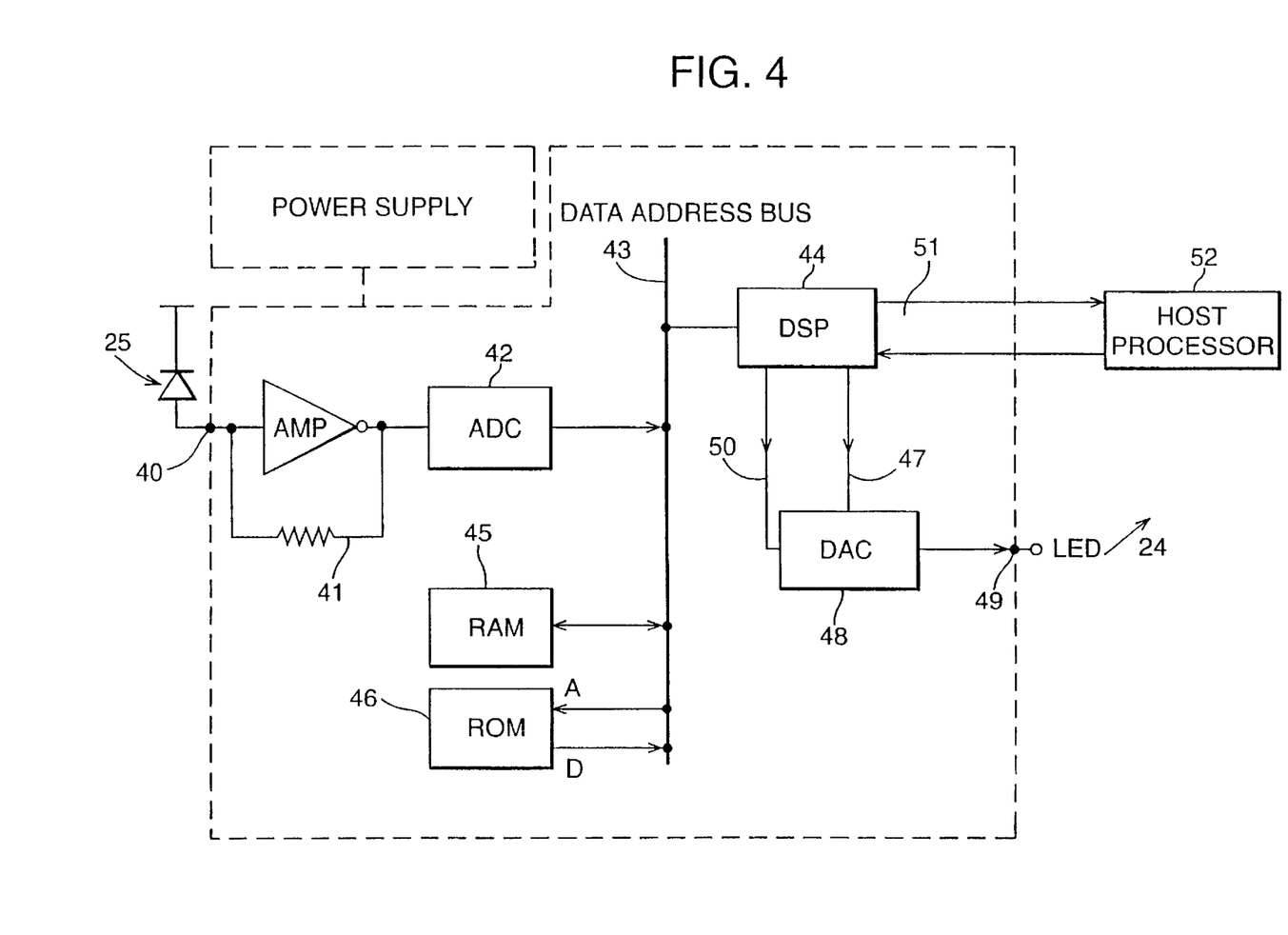
FIG. 4 is a circuit diagram of a processing circuit associated with the embodiment of FIG. 3.

Referring now to FIG. 4 of the accompanying drawings, this shows the light sensor 25 connected to the input of the control circuit. This input is indicated at 40 and leads to an operational amplifier circuit 41, the output of which is taken to an analog-to-digital (ADC) converter 42, in turn connected to a data bus 43 The datastream coming from the ADC 42 is processed in a digital signal processor (DSP). A suitable processor is the TMS320C32 manufactured by Texas Instruments. Working area for the DSP 44 is provided by a RAM 45 and the circuit also includes a ROM 46 which can be accessed by the DSP 44 in order to carry out steps of the processing which will be described hereinafter.

Apart from its major function the DSP 44 controls the OFF and ON switching of the LED 24. In operation the LED emits continuously.

Before the major function of the DSP 44 will be described, a minor function that it carries out is the calibration of the light pulses supplied by the LED 24 to the measurement volume. The generation of these light pulses is controlled by signals on a line 47 to a digital-to-analog converter (DAC) 48 connected via an output 49 to the LED 24. The level of the output of LED 24 is set by control signals on a line 50 also connected to DAC 48. At predetermined intervals the DSP 44 will cause the LED 24 to emit a series of short calibration pulses, the presence of which, and level of which, will be detected by the sensor 25 and utilised to set the post ADC gain during normal measurement. In the present embodiment the outputs of the DSP 44 are connected by serial links 51 to a host processor indicated at 52. This host processor may be a personal computer or a laptop or a specific terminal configured purely for carrying out the purposes of the present invention.

Figure 5:
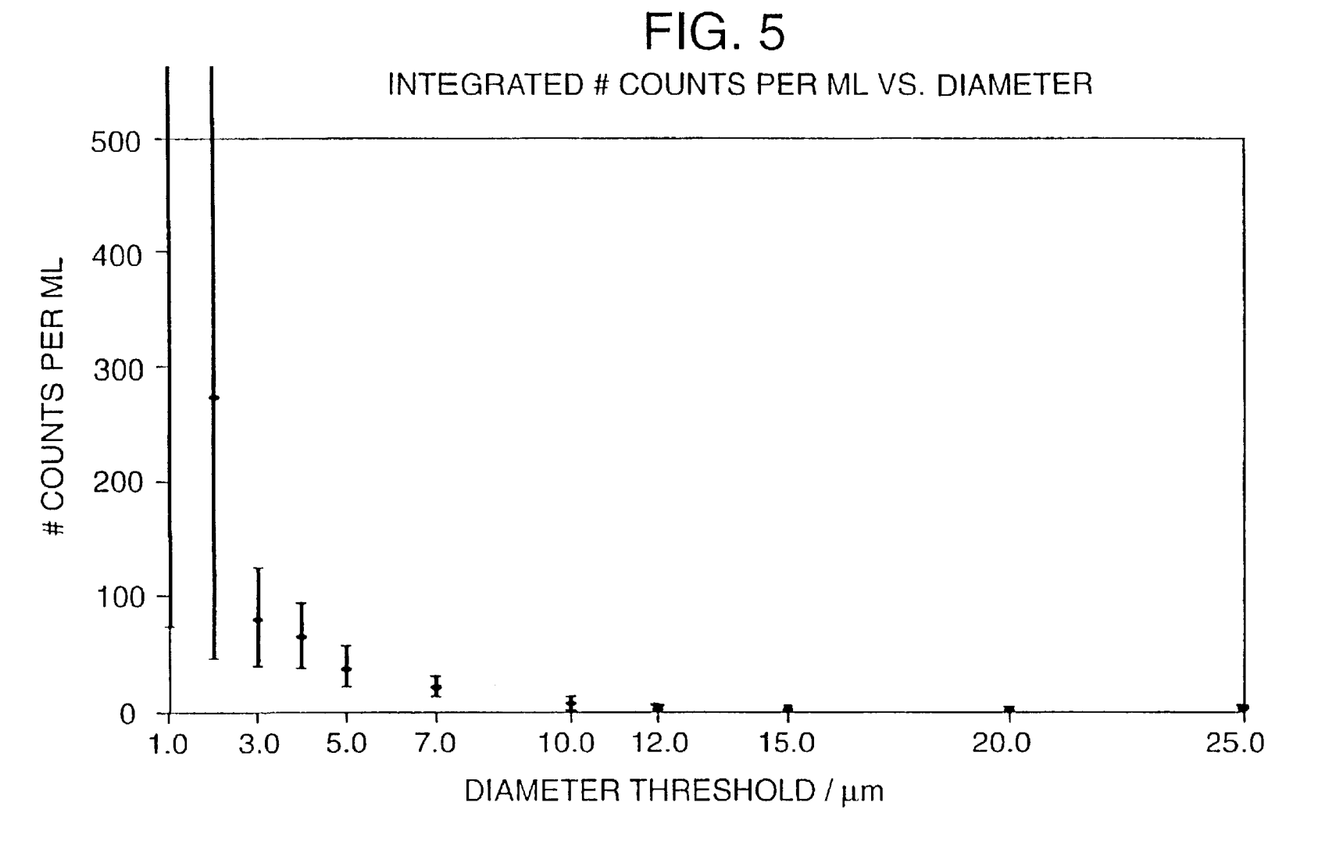
FIG. 5 is a print out of particle measurements carried out with the apparatus of FIGS. 3 and 4.

Once the data has been finally processed by the host processor 22, it can be either displayed or printed for further use. FIG. 5 shows a typical printout which may be obtained. This figure will be described in greater detail hereinafter.

It will be appreciated that the computational process is carried out on intermittent streams of digital data leaving the ADC 42 caused by particles moving through the measurement volume through the light field generated by the DSP 44 intermittently actuating the LED 24. The ADC acts by sampling the analog input supplied to it and in the present embodiment generates frames of data. For example, in the present embodiment an output similar to that shown in FIG. 2A is sampled to generate a frame having 48 samples of 10 bit data. In the embodiment being described the computations required are such that this volume of data cannot be handled without exceptionally extensive data processing resources. Accordingly the present embodiment carries out a data reduction step on the sampled data. In this data reduction step the 48 samples of a frame of interest are reduced to a simple 15 bit number D composed of quantised transformed log moments. This data reduction step is one of three important steps to be carried out during the measurement process which will be described in greater detail hereinafter. However, it will be appreciated that the actual sampling and reduction parameters can be varied. Additionally, the data reduction step is triggered by the detection that the energy of the signal being sampled is above a predetermined threshold and thus indicating the presence of an event, in this case a particle, passing through the measurement volume.

The ROM 46 stores a look up table with estimated values for the probability $P(D|\theta)$ for each value of D so obtained, and for $\theta$, where $\theta$ represents the particle radius and velocity parameters that may be more or less likely to have caused the observation of D. The generation of the look-up table is a second important step.

The third step is an inferential processing step using Bayesian inference in which the distribution of $\theta$ is inferred from the sequence of D values observed and the prior distribution of $\theta$.

The computations and actions required to carry out these three steps will now be described in general terms, bearing in mind that the specific embodiment shown in FIGS. 3 and 4 for measuring particles using structured light is only one embodiment. Thus there are many other systems which could produce analog or digital data from unobservable phenomena which could be analysed to produce valuable results by the same computational process.

Figure 6A:
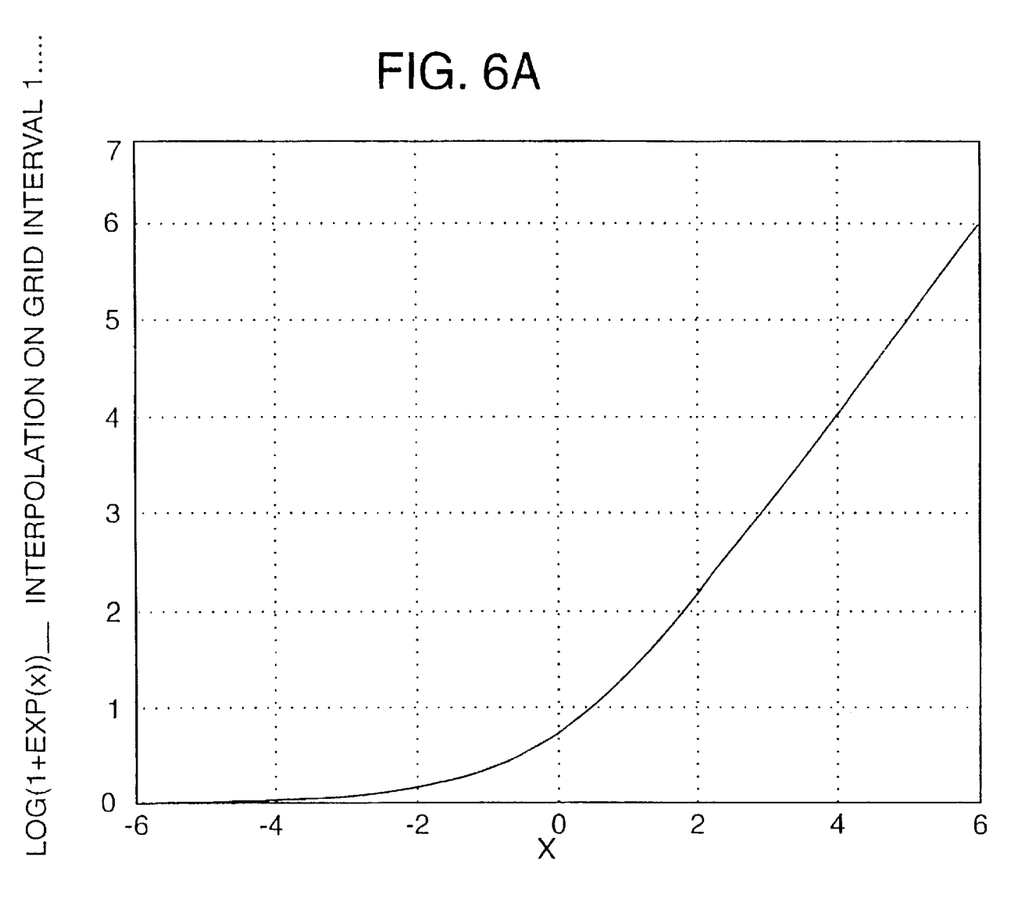
FIGS. 6A and 6B are graphs of functions of which are of particular importance when the processing to be described hereinafter is carried out.

During the subsequent description the processing probabilities may be expressed in one of three forms, which are interconvertible and have different merits. The three forms are probability, log probability, and log odds. Probability and log probability are self-explanatory; if p is a probability, the corresponding log odds is the quantity $\log(p/(1-p))$. If x is the log odds, the corresponding probability is $e^x/(1+e^x)$. Another function which will be utilised in the subsequent description is the function $f(x)=\log(1+e^x)$. This function is frequently used during the processing to be described and is used in the majority of instances in situations where its value at a series of regularly spaced values of x is needed where the spacing interval is $x_0$. This function is shown in FIG. 6A and a very close approximation can be obtained by storing a look-up table on an $x_1=0.1$ interval grid and linearly interpolating. In the case where the interval $x_0$ is a small multiple of $x_1$ a series of values can be obtained and added to another array is only three cycles of a computational algorithm. The function f(x) can also be utilised in adding a set of numbers expressed as their logs. Thus given $a=\log(A)$ and $b=\log(B)$ it can be noted that $\log(A)+(B)=a+f(b-a)$ without the need to exponentiate or otherwise take logarithms. Repetition of this operation adds a whole set of such numbers yielding the logarithm of the sum.

This function has two main uses. Firstly it can be used for converting from log odds to log probability. Thus if $x=\log(p/(1-p))$, then $p=e^x/(1+e^x)$, and $\log(p)=x-f(x)$. Secondly in carrying out conversions from log odds to log(1- probability). Thus if $x=\log(p/(1-p))$, then $\log(1-p)=-f(x)$.

Figure 6B:
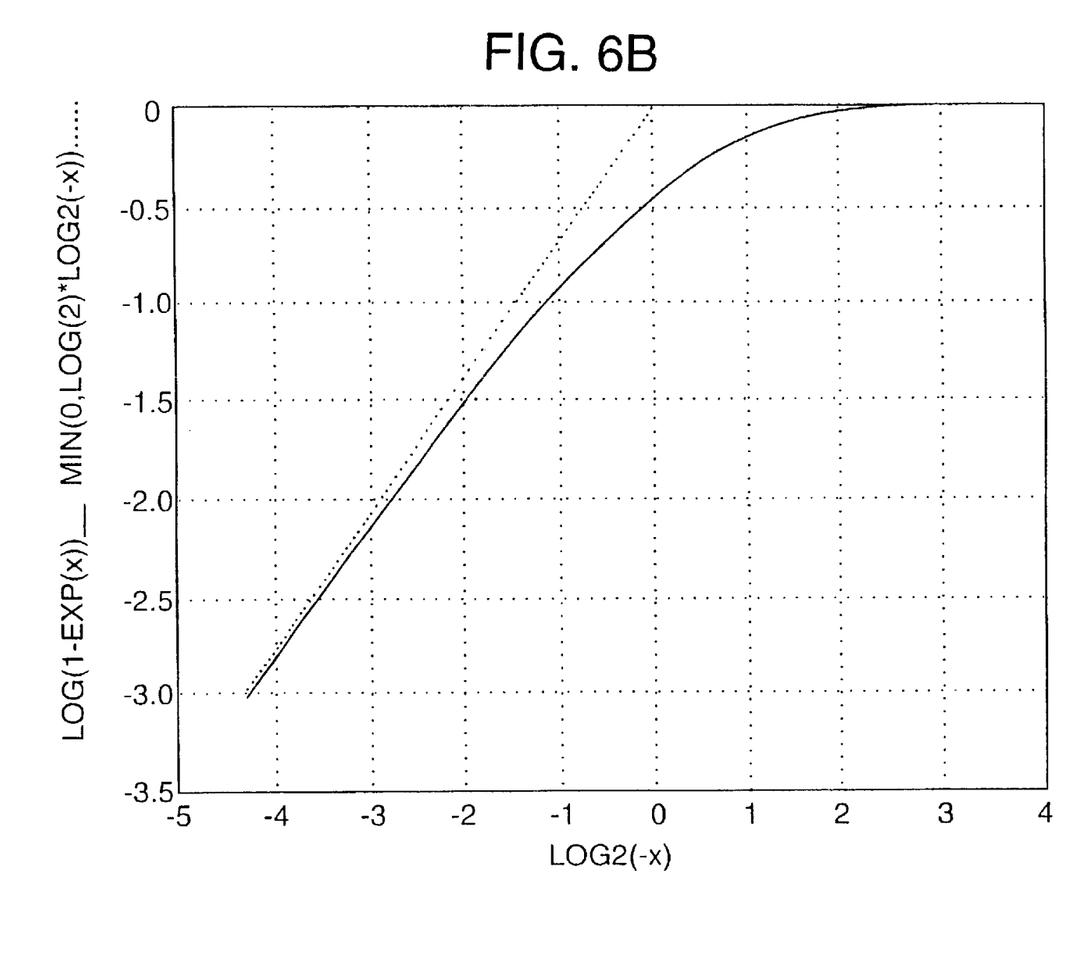

A second function of importance in the following calculations is shown in FIG. 6B. This is the function $h(x)=\log(1-e^x)$. This function is used in the range $x<0$ only. It is less well behaved than f(x) in that it has an essential singularity and branch point at one end of the range. In the following computations it is used less frequently than f(x). The integer part of $\log(-x)$ can be extracted by reading the exponent part of the floating point representation of x. When h(x) is plotted against $\log_2(-x)$ it is seen that only a short look up table is required for h(x) to cover small absolute values, with h(x) at large absolute values of $\log_2(-x)$ being well approximated by $\log(2)*\log_2(-x)$ when $\log_2(x)$ is negative and by zero when $\log_2(-x)$ is positive.

Thus for different ranges of their function
a) $x \leq -20$: $h(x)=0$
b) $-20 \leq x \leq -0.1$: h(x) is obtained by interpolation in a table of interval 0.1
c) $-0.1 \leq x$: h(x) is obtained by interpolation in an effective table of entries at values of x of the form of $-2^{-n}$ for positive integer n, where the table values are actually given by the formula $-n \log(2)$.

In the following description this function has the following uses. Firstly computing log(1-p) from log(p). Thus if $x=\log(p)$ then $\log(1-p)=h(x)$. Secondly computing log odds from log probability. Thus if $x=\log(p)$ then $\log(p/(1-p))=x-h(x)$.

Having now set out what are in essence the building blocks of the processes to be described hereinafter there will now be given a description in general terms of the computational procedures carried out by the DSP 44, and in particular to the three steps which have already been referred to.

The inferential computations will now be described in a general form which is nevertheless applicable to the embodiment of FIGS. 3 and 4.

Thus for the measurement of particle radii there is provided a set of bins of particle radius values centerd on the values $r_i$ for $i=1, \ldots, I_1$. These bins are of course dependent on the expected range of particle values for a particular application.

Similarly a set of bins are provided for the measurement of particle velocity centerd on the values $v_i$ for $i=1, \ldots, I_2$, which are similarly dependent on the particular application.

For each combination of r and v there is then an event type $E_i$, where $1 \leq i \leq I_1 I_2$, which indicates that a particle size of r and velocity v passed through the sensitive volume for that particle size during a particular frame. The type of $D_j$ that results depends on the noise present and on the z and y coordinates with which the particle transited, but is governed by the probabilities $P(D_j|E_i)$. The probability of each $E_i$ occurring depends on the fluid being assessed, and for any particular fluid is given by $p_i$.

Nonetheless the invention is more generally applicable to situations where the non-directly-observable events $E_i$ are not related to particles or their radius and velocity.

Given any particular fluid of "homogeneous" article concentration in which the particles to be measured are carried there is associated with it a set of probabilities $p_i$ that when passed through the particle counter for one frame, which in the present embodiment is an interval of 62 $\mu$s corresponding to the maximum time of transit of the largest expected particle at the lowest expected velocity, a particle of radius in the bin centered on $r_i$ passes through the predefined "active volume" of the sensor, where the active volume may depend on i. It is assumed that there is negligible probability of two such events occurring in the same frame, and that one of the $r_i$, say $r_0$, is zero, representing the possibility that there is no particle in the frame. Clearly then $\Sigma p_i = 1$.

Now, when a given fluid with assumed stationary input particle distribution (and hence fixed vector p whose components are the $p_i$) is connected to the sensor it is possible to have some prior idea what sort of values the vector p is likely to take. This prior idea is expressed in the form of a prior distribution on p, which is denoted P(p). This distribution will have the property that for p whose components do not sum to 1, P(p) will be zero, while the I-1 dimensional integral $\int P(p)dp=1$. It may be broad and flat indicating that there are no preconceived ideas as to what sort of fluid is to be looked at, or it may be restricted and narrow indicating that there is already a pretty good idea of what sort of fluid it is because it has already been processed in some way and experience has been gathered on what sort of fluid is to be examined.

P(p) thus represents the input particle size distribution which as discussed does not represent an actual measurement. After each trigger (or indeed after some defined time period with no trigger) there is generated some data D (which here represents the calculated moments rather than the full data trace), and the first stage of the inference process has obtained the values of $$\log\left(\frac{P(D\mid E_i)}{\sum_i (P(D\mid E_i))}\right)$$

What is required in order to provide a measurement is to infer the posterior distribution of p, given the data, P(p|D), which will then become the prior distribution for the processing of the next trigger or tick. When the measurement process is over the final posterior distribution after the last trigger was processed is the final posterior particle size distribution that is available for display in whatever complete or simplified way is required; it will reflect not only what the concentration of particles at each bin size is, but also the degree of certainty with which the results are presented. It is this inference of the posterior distribution of p from the prior distribution of p for each trigger that is the task of the update process to be described.

For the purposes of this embodiment it is always considered that the original prior distribution before any data is examined will be a Dirichlet distribution, given by $$P\left(p\mid \sum_i p_i\right) = \frac{\Gamma\left(\sum_i \alpha_i\right)}{\prod_i \Gamma(\alpha_i)} \prod_i p_i^{\alpha_i - 1},$$

where all $\alpha_i > 0$, because (a) it is easy to work with, (b) it is the natural class of distributions that arises from already having made some measurements on the fluid in question having previously had no idea about it, and (c) it allows all the likely types of priors which may be of interest by suitable variation of the parameters $\alpha_i$. For actual determination of a suitable set of $\alpha_i$ for a particular application either a guess may be taken based on intuition (including the totally flat prior ($\alpha_i=1$ for all i), or a number of fluids can be assessed on the basis of a totally flat prior, and inference made on the $\alpha_i$ using an appropriate Bayesian inference method.

One of the particular points about a Dirichlet that is helpful is that the complete distribution P(p) is defined by its marginal distributions $P(p_i)$. Note that the Dirichlet is not a separable distribution; it is not stated that $P(p)=\Pi P(p_i)$. It suffices rather, given a Dirichlet distribution, to record only the marginal distributions to define the whole distribution with potential savings of memory. The difficulty that prevents the simple recording of the $\alpha_i$ (with a huge saving in memory and computation), is that the first stage inference is uncertain—complete certainty in the first stage inference would allow only recording the $\alpha_i$, as the distribution remains a Dirichlet distribution after each trigger is processed. In this instance, it becomes instead a mixture of an increasingly large number of Dirichlet distributions; yet although recording of the $\alpha_i$ is no longer sufficient, recording of the marginal distributions $P(p_i)$ is sufficient given an approximation described hereinafter.

Thus, there exists an unknown probability vector P, with components $(p_i)_{i=1,\ldots,I}$, such that $$\sum_{i=1}^{I} p_i = 1$$

corresponding to a set of I mutually exclusive events $(E_i)_{i=1,\ldots,I}$ which are not directly observable, one of which occurs in each time period $E_i$ with the probability $P_i$. Each of these events corresponds, for example, to the passage of a particle through the structured light field shown in FIG. 1A. There is also provided a known matrix A, and a set of mutually exclusive observable events $(D_j)_{j=1,\ldots,J}$, one of which occurs in each time period. The matrix A has components $(a_{i,j},\ldots,j=i,\ldots,J)_{i=1,\ldots}$ which are the values of the conditional probabilities $P(D_j|E_i)=a_{i,j}$. For any one time period, D may be assumed to be conditionally independent of p given E, and E for one time period may be assumed to be conditionally independent of E for any other time period given p.

As already stated in order to carry out meaningful calculations it is also necessary to have a prior set distribution P(p) on p. The purpose of the computation to be described in the following is to take this prior set distribution, in general terms P(p) and in effect carry out an iterative process on each subsequent set of measurements so as to eventually reach the most probable distribution of the events that have occurred. Thus the underlying task is to infer the posterior distribution P(p|D), where $D=(D_{jk})_{k=1,\ldots,K}$ is the sequence of observed events. In particular, the processing is directed towards identifying its marginal distributions $P(p_i|D)$.

Thus the present embodiment carries out an algorithm which updates the prior marginal distributions $P(p_i)$ to get the posterior marginal distributions $P(p_i|D_{ji})$ that result after a single time period. This step can then be repeated once for each time period, the posterior from each time period being used as the prior for the next.

This algorithm involves the set of equations listed in Appendix A as set 1.

All equations or lists of equations referred to by numbers in this specification are set out in Appendix A attached to the end of this specific description.

In the last line of the equations in set 1 the approximation has been made $$P(E_h|\bar{E}_i,p_i) \approx P(E_h|\bar{E}_i) \text{ for } h \neq i.$$

which is an exact equality if the prior on p is a Dirichlet distribution. For arbitrary mixtures of Dirichlets this may be far from the truth. However, in practice the approximation can be shown to provide excellent results for the set of Dirichlets that arise in practice. The above derivations are continued as shown in the set of equations 2 of Appendix A. In the last equation of this set $f(x)=\log(1+e^x)$ and K is some constant whose value is unimportant; it is known that $\int P(p_i|D)dp_i=1$, so the value of K can be determined later. In practice the stored values of K are set to keep the stored values of log $P(p_i|D)$ in reasonable range.

In practice the value of log $P(p_i|D)$ cannot be stored for every possible value of $p_i$, so there is chosen an appropriate set of values of $p_i$ for which is remembered log $P(p_i|D)$. Suppose there are M such points. Then the above expression has to be evaluated MI times for each time period. These evaluations are carried out by the DSP 44 of FIG. 4.

By making one further approximation the computation can be so organised that each evaluation of MI needs take only slightly more than three CPU cycles on a processor such as the DSP 44.

In carrying out the evaluations it is noted that $P(D_j|E_i)=a_{i,j}$. For each $p_i$, there is selected a set of values $q_{i,k}$ such that the values of $$\log\frac{q_{i,k}}{1-q_{i,k}}$$

as k varies are uniformly spaced, and at any time the values of log $P(p_i|D)$ for $p_i=q_{i,k}$ for each k are remembered.

The function f above is implemented using interpolation in the look-up table stored in ROM 46;

f is used to perform the summation over h in the log domain;

the values of $$\log\frac{P(E_i)}{1-P(E_i)}$$

are only updated once every N time periods, for some integer N of the order of 20 (this effectively introduces a further approximation);

The updates to $P(q_{i,k}|D)$ are combined for several successive time periods, in order to increase efficiency.

In carrying out the above calculation some approximations have been made:

1. $P(p)$ is adequately represented by its marginals $P(p_i)$ in the same way that a Dirichlet distribution is, to be precise, that $P(E_h|E_i, p_i) \approx P(E_h|E_i)$ for $h \neq i$.
2. $P(p_i)$ is adequately represented by its values on the points $p_i=q_k$, where $q_k$ are a set of probabilities whose corresponding log odds values $a_k$ are evenly spaced over some interval;
3. $P(E_i)$ changes sufficiently slowly that for the purposes of updating $P(p_i|D)$ it may be reevaluated after every N time periods rather after every time period, where roughly speaking $N \leq 20$.

In the previous section it was assumed that the values in the matrix A were known. This matrix A is effectively the look-up table (LUT) which is stored in ROM 46 of FIG. 4 and is referred to in step S2 of the flow diagram of FIG. 7. However, determining these values is one of the tasks to be performed in most situations where the methods of the previous section would be needed, and in particular in the particles sizer shown in FIGS. 3 and 4.

Two possible approaches for filling the look-up table are: firstly simulate the hardware in such a way that the normally unobservable events $E_i$ can be caused to occur during each time period at will; use the simulation to determine the value of $D_j$ that occurs for each time period, and hence infer the maximum a posteriori or alternatively the mean posterior values of the elements of A or secondly use the actual hardware under circumstances where the value of p is known (or, failing that, where a distribution of the possible values for p is known), collecting the numbers of each $D_j$ that occur, and hence infer A as will be described.

It is of course possible to provide hybrid methods which combine the features of each of the above steps.

The best technique known at present is to set the prior distribution of A as Dirichlet as follows. Let a now be the probability vector for the various possible values of D that occur for a given E (which is now considered fixed). This is given a prior Dirichlet distribution by setting $$P(a) = \begin{cases} \frac{\Gamma\sum_j(\alpha_j)}{\prod_j\Gamma(\alpha_j)}\Gamma ja_j^{\alpha_j-1} & \text{if } \sum_j(\alpha_j) = 1 \\ 0 & \text{if } \sum_j(\alpha_j) \neq 1 \end{cases}$$

where all the $\alpha_j$ are equal, positive, and in turn have prior distribution set (for example) by $P(\alpha)=\beta e^{\beta\alpha}$ for some positive constant $\beta$ of magnitude not far from 1.

Let it be supposed that $n_j$ occurrences of $D_j$ are observed during each time period in which E is true, and that $N=\Sigma n_j$. Then the various alternative values that can be taken for $a_j$ are:

a) The maximum likelihood value: $a_j=n_j/N$;
b) The mean posterior value, which for any fixed value of $\alpha$ is given by $$a_j = \frac{n_j + \alpha}{N\alpha},$$

and which for general alpha drawn from the prior may be determined using (for example) Markov Chain Monte Carlo methods;

c) The modal posterior value, which may be obtained by using any standard optimisation technique on the posterior distribution $P(a,\alpha)=QP(\alpha)P(a|\alpha)Pn|a,\alpha)$ for some unimportant constant Q;

d) The mean posterior value of a for the modal posterior value of $\alpha$.

The second approach is relatively laborious.

It is required that the equipment be set up in such a way that (at different times) the probability vector p takes on a number of known values, say $q_k=(q_{k,i})$.

Let $a_{i,j}$ be the probability of getting $D_j$ given $E_i$, and $n_{j,k}$ be the number of times during the running of the kth setup that $D_j$ is observed. Let A denote the matrix consisting of the $a_{i,j}$'s.

First a prior distribution on A has to be chosen. A recommendation is a Dirichlet of the same type used in the preceding section.

The mean posterior value of A is then inferred, given the data $N=(n_{j,k})$.

The likelihood of N given A is given by the set of equations 3 in Appendix A. Now, it is noted that $P(A)=0$ unless $(\forall i)\Sigma a_{i,j}=1$. Monte Carlo Markov Chain Methods are used to determine the mean of the posterior, so random samples are drawn from $P(A|N)$. In order to make this easier given the restrictions on A, there is written $a_{i,j}=b_{i,j}/c_i$, where $c_i=\Sigma b_{i,j}$, and instead of sampling from $P(A|N)$, sampling is carried out from $P(A,c|N)$, where $P(c|A,N)=P(c)$ which is Gaussian. This can be achieved by (in random order) Metropolis sampling from the conditional distributions $$P(b_{i0},j_0,c_{i0}|(a_{i,j})(i,j)\neq(i_0,j_0),N,Q,(c_i)_{i \neq i0})$$

and $$P(c_{i0},j|A,N,Q,(c_i)_{i \neq i0})=P(c_{i0}).$$

for all possible values of $i_o$

It is of course necessary to arrive at values for D to enable the foregoing calculation to be carried out. In the present embodiment this involves the data reduction step already referred to and will now be described in greater detail.

Thus the symbols $E_i$ in the above descriptions correspond in the actual implementation under consideration to the events "a particle of a particular size travelling at a particular velocity was present in the sensitive volume appropriate to that size and velocity during the time period under consideration", where the index i varies with the size and velocity in question, with one or more values of i indicating that no particle fulfilled these conditions during the time period under consideration.

The actual events referred to as $D_j$ above might in theory be the data signal recorded during a given time period. In practice, however, such a data signal contains too much information to process in the time available. The $D_j$ observed are therefore a "digested" version of the said data signal. The method used to "digest" them in this particular implementation will now be described in greater detail.

The particular "digestion" or data reduction method used is to take the data signal consisting of ADC samples $y=(y_m)_{m=1}, \ldots, _M$, and make the calculations set in the set of equations 4 in Appendix A where T is an empirically determined matrix. Then the D value corresponding to y is a quantised version of v.

The design rationale being employed here is that the set of values $u_1, u_2, u_3, u_4, \ldots$ completely determine the set of values $\{y_i, \ldots y_m\}$, and that the $u_1', u_2', u_3', u_4', \ldots$ completely determine the set of values of $\{z_1, \ldots z_m\}$; both together go a long way towards determining the vector y. The manner in which this determination occurs is that the successive $u_n$ values determine the successive derivatives at the origin of the spectrum of the (order independent) distribution of $y_m$ values. If it is wanted to retain a small amount of information about y in a diffuse rather than local manner, u is one possible way of doing it.

The purpose of T and t are to minimise the loss of information due to quantisation; T and t are chosen empirically for this purpose based on the range of values of v that are observed during typical (possibly simulated) data collection.

Figure 7:
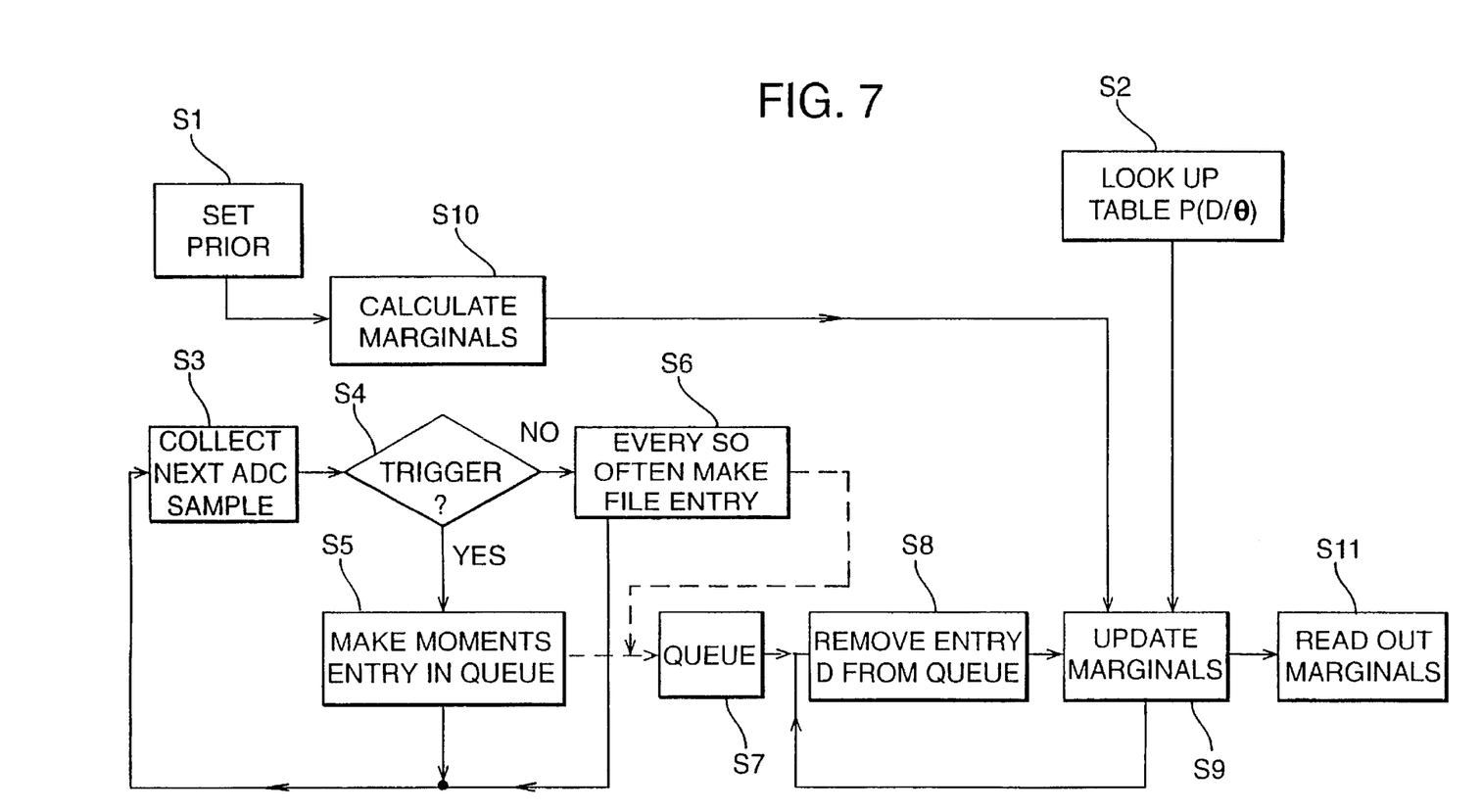
FIG. 7 is a flow diagram setting out the computations carried out by the circuit of FIG. 4.

Returning now to the flow diagram of FIG. 7 it will be appreciated from the foregoing that two steps have to be taken before the actual calculations on real events can be carried out. These prior steps are shown in FIG. 7 at S1 and S2. At step S1 the prior is set. As explained already the prior is in Dirichlet form or is a mixture of a well behaved set of Dirichlets. In step S2 the contents of the look-up table stored in ROM 46 are calculated as already described. Once the prior has been set and the look-up table filled the actual process of measurement can begin using the apparatus described in general terms in FIGS. 1 and 2 and in greater details in FIGS. 3 and 4.

Thus at step S3 a sample is taken from the output of ADC 42 (FIG. 4). This sampling is carried out at regular intervals which in the present embodiment is every $\frac{1}{780000}$ of a second. Naturally this may well vary if different events are being measured. The sampled data from the ADC is supplied to a trigger in step S4. In the present embodiment the trigger decides if the energy content in the sample is significant or not. If the energy content is significant, which may in the present embodiment corresponds to the passage of a particle through the measurement zone, the signal is reduced in the manner already described to provide a 15 bit number D. This number is entered at step S5 in a data queue. The fact that no significant signals are occurring is also of interest. If the fluid flow is particularly clear then triggered events will be sparse. Thus every predetermined period a tick entry is entered in the data queue. This is done at step S6. The resulting Queue is indicated at S7. At step S5 the oldest entry is removed from the queue and at steps 9 the Bayesian inference step already described is carried out utilising initial marginals calculated in step 10 from the prior set in step 1 and with reference to the look-up table set up in step S2. As already described in step S9 the prior marginal distribution $P(p_i)$ are updated to get the posterior marginal distributions $P(p_i|D_{jk})$ that result after a single time period.

Essentially step S9 comprises two inferential subprocesses. The first of these is to access the LUT set up in step S2. This access is dependent on the value of the entry removed from the queue in step S8. As described in the part of the specification dealing with the compression of the data taken from the ADC, $D_{jk}$ can be expressed in terms of $u_2, u_3, u_2'$ and the values $u_2, u_3$ and $u_2'$ or alternatively their transformed quantized counterparts are used to determine whether the LUT hold the values of $a_{i,j,k}$ or not. If for a value $D_{jk} u_2'$ lies outside a particular range dependent on $u_2$ and $u_3$ then the LUT returns a standard set of equal values.

This can be done if the data is stored in the LUT in compressed form as it has been found that a complete table actually contains many duplicated values.

If $u_2'$ lies within the range then the set of 187 1-byte values for log odds of $$\frac{P(D|E_i)}{\sum_i P(D|E_i)}.$$

The decompressed log odds so obtained are then converted to log probabilities using function f(x) shown in FIG. 5A. The second set of inferential processes is the Bayesian inference procedure already described in the present specification. The result of each step of this process is a marginal distribution which can be read out in steps 11 and displayed or printed and an example of which is shown in the graph of FIG. 5.

Each of the points on the graph refers to one of the bins for a particular range of particle radii already referred to in this description. Thus according to the graph over the period of the measurement the probability was that there were over $10^3$ counts of particles per milliliter of the smallest size bin, 280 counts of particles per milliliter of the next sized bin and so on. It has to be emphasised that these are not actual counts but a representation of the probability distribution of the particles which caused events in the flow chart of FIG. 6. As these points actually represent probabilities it does not mean that there were actually $10^3$ particles in the first "bin". In fact upper and lower confidence factors are also given to the points which will indicate that there may be fewer or more counts in each bin. However the actual graph is a very clear representation giving a considerable amount of information. The lower and upper ends of the bar indicates that the posterior probability of the concentration of particles in that bin being in the range indicated is 0.9. This figure can be adjusted up or down giving a wider or narrower range.

It will be appreciated that the above description has been given with regard to particles moving through a light beam so as to cause perturbations which are subsequently detected. However as already mentioned the statistical algorithm described in the present specification is capable of application in other fields. A simple example of this is that it might be desired, for management purposes, to measure the use to which a digital data link is being put without being allowed, for example for security of confidentiality reasons, to access the actual data being transmitted. Thus it might be required to measure how many of the packets transmitted over the link represent uncompressed video, how many uncompressed audio, how many MPEG compressed video, how many ASCII text and so on. As the data itself cannot be accessed the only data available to be used in making the measurements is the check sums and lengths of the packets.

Following the procedure already described $E_1$ can be allocated to the event that an uncompressed video packet was sent, $E_2$ the event that an uncompressed audio packet was sent and so on for each of the packet types. Additionally $P_1$, $P_2$ etc represent the true values of the probabilities of the different types of packet being sent.

It is now possible to form the matrix of probabilities $P(D_j|E_i)=A_{i,j}$ by a study of the check sums and lengths of packets that have been transmitted by a known source. Each set of data, that is each check sum and length pair, $D_j$, can be observed and from this there can be inferred by the method already described the posterior distributions $P(p_i|D_1.D_2 \ldots D_N)$. Thus the user can determine how likely it is that each packet transmitted is video, audio etc and how certain these probabilities are.

APPENDIX A

EQUATIONS 1

$$P(p_i | D_{j_1}) = \frac{P(p_i)P(D_{j_1} | p_i)}{\int \text{numerator } d p_i}$$

$$= \frac{P(p_i)(P(D_{j_1} | E_i)P(E_i | p_i) + P(D_{j_1} | \overline{E}_i, p_i)P(\overline{E}_i | p_i))}{\int \text{numerator} d p_i}$$

(where $\overline{E}_i$ denotes "not $E_i$")

$$= \frac{P(p_i)(P(D_{j_1} | E_i)p_i + (1 - p_i)P(D_{j_1} | \overline{E}_i, p_i))}{\int \text{numerator } d p_i}$$

$$= \frac{P(p_i)\left(P(D_{j_1} | E_i)p_i + (1 - p_i)\sum_{h \neq i} P(D_{j_1} | E_h, \overline{E}_i, p_i)P(E_h | \overline{E}_i, p_i)\right)}{\int \text{numerator } d p_i}$$

$$= \frac{P(p_i)\left(P(D_{j_1} | E_i)p_i + (1 - p_i)\sum_{h \neq i} P(D | E_h, p_i)P(E_h | \overline{E}_i, p_i)\right)}{\int \text{numerator } d p_i}$$

(since $(h \neq i \wedge E_h) \Rightarrow \overline{E}_i$)

$$= \frac{P(p_i)\left(P(D_{j_1} | E_i)p_i + (1 - p_i)\sum_{h \neq i} P(D_{j_1} | E_h)P(E_h | \overline{E}_i, p_i)\right)}{\int \text{numerator } d p_i}$$

(since $D$ is conditionally independent of $p$ given $E$)

$$\approx \frac{P(p_i)\left(P(D_{j_1} | E_i)p_i + (1 - p_i)\sum_{h \neq i} P(D_{j_1} | E_h)P(E_h | \overline{E}_i)\right)}{\int \text{numerator } d p_i}.$$

APPENDIX A $$P(p_i \mid D_{j_1}) = \frac{P(p_i)\left(P(D_{j_1} \mid E_i)p_i + (1-p_i)\sum_{h\neq i} P(D_{j_1} \mid E_h)\frac{P(E_h, \overline{E_i})}{P(\overline{E_i})}\right)}{\int \text{numerator } d\,p_i}$$

$$= \frac{P(p_i)\left(P(D_{j_1} \mid E_i)p_i + (1-p_i)\sum_{h\neq i} P(D_{j_1} \mid E_h)\frac{P(E_h)}{1-P(E_i)}\right)}{\int \text{numerator } d\,p_i}$$

(since $(h \neq i \wedge E_h) \Rightarrow \overline{E_i}$)

$$= \frac{P(p_i)(1-p_i)\left(P(D_{j_1} \mid E_i)P(E_i)\frac{1-P(E_i)}{P(E_i)}\frac{p_i}{1-p_i} + \sum_{h\neq i} P(D_{j_1} \mid E_h)P(E_h)\right)}{\int \text{numerator } d\,p_i}$$

(since mutiplication of the numerator by a constant,
in particular by $(1-P(E_i))$, changes nothing by
virtue of the denominator)

$$= \frac{P(p_i)(1-p_i)\left(\frac{P(D_{j_1} \mid E_i)P(E_i)}{\sum_{h\neq i} P(D_{j_1} \mid E_h)P(E_h)}\frac{1-P(E_i)}{P(E_i)}\frac{p_i}{1-p_i} + 1\right)}{\int \text{numerator } d\,p_i}$$

Therefore $$\log P(p_i \mid D) = \log P(p_i) + \log(1-p_i) +$$

$$f\left(\log\frac{p_i}{1-p_i} - \log\frac{P(E_i)}{1-P(E_i)} + \log\left(\frac{P(D_{j_1} \mid E_i)P(E_i)}{\sum_{h\neq i} P(D_{j_1} \mid E_h)P(E_h)}\right)\right) + K$$

EQUATIONS 2

APPENDIX A $$P(N \mid A) \propto \prod_k P\big((n_{j,k})_j \mid A\big)$$

$$= \prod_k \prod_j \left(\sum_i P(D_j, E_i \mid A)\right)^{n_{j,k}}$$

$$= \prod_k \prod_j \left(\sum_i q_{i,k} a_{i,j}\right)^{n_{j,k}}$$

EQUATIONS 3

$$\overline{y} = \frac{1}{M}\sum_{m=1}^{M} y_m$$

$$u_n = \frac{1}{M}\sum_{m=1}^{M} (y_m - \overline{y})^n$$

$$z_m = y_{m+1} - y_m$$

$$\overline{z} = \frac{1}{M-1}\sum_{m=1}^{M-1} z_m$$

$$u'_n = \frac{1}{M-1}\sum_{m=1}^{M-1} (z_m - \overline{z})^2$$

$$u = \begin{pmatrix} \log|u_2| \\ \log|u_3| \\ \log|u'_2| \end{pmatrix}$$

$$v = Tu + t$$

EQUATIONS 4

What is claimed is:

1. Apparatus for obtaining a posterior probability distribution $P(p|D)$ relating to an attribute or attributes $\theta$ quantized into I values $(\theta_1, \ldots, \theta_I)$ of a succession of events each one of which is one of the types $(E_1, E_2, \ldots, E_I)$ in which the events generate measurable physical reactions, the posterior probability distribution $P(p|D)$ being on a distribution $P(\theta)$ of $\theta$, where $P(\theta)$ is represented by $p=(p_1, p_2, \ldots p_I)$ where $p_i=P(\theta_i)$; the apparatus comprising:

means for detecting the physical reactions generated by the events and generating measurements $D=(D_1, D_2, \ldots, D_j, \ldots)$ in response to the detected reactions; and inferential processing means for deriving values $P(p_i=q_{i,k}|D)$ at points $q_{i,k}$ of the marginal distributions $P(p_i|D)$ of the probability distribution $P(p|D)$ for the distribution of the attribute or attributes $\theta$ of the events by carrying out a Bayesian inferential process utilising the values $(D_1, D_2, \ldots D_j, \ldots)$, the marginal values $P(p_i=q_{i,k})$ of a preset prior probability distribution $P(p)$ which marginal values define the complete preset prior probability distribution, and a stored set of values $P(D_j|E_i)$ representing a range of probability distributions for the occurrence of each of the observed measurements D from the events of each type of E occurring, the inferential process being an iterative process in which the values $P(p_i=q_{i,k}|D_1, \ldots, D_j)$ of the marginals $P(p_i|D_1, \ldots, D_j)$ after the jth event are generated from the values $P(p_i=q_{i,k}|D_1, \ldots, D_{j-1})$ of the marginals $P(p_i|D_1, \ldots, D_{j-1})$ prior to that event.

2. Apparatus according to claim 1, wherein the generating means are adapted to generate an analog signal and include analog-to-digital conversion means for converting the analog signal into a digital signal and means for compressing the data content of the digital, the output of said compression means being connected to said processing means.

3. Apparatus according to claim 2, wherein the compression means are adapted to compress the digital output of the ADC means to generate the value D by taking quantized transformed log moments.

4. Apparatus according to claim 3, wherein the compression means obtain the quantized transformed log moments by carrying out the steps set out as follows:

$$\bar{y} = \frac{1}{M}\sum_{m=1}^{M} y_m$$

$$u_n = \frac{1}{M}\sum_{m=1}^{M} (y_m - \bar{y})^n$$

$$z_m = y_{m+1} - y_m$$

$$\bar{z} = \frac{1}{M-1}\sum_{m=1}^{M-1} z_m$$

$$u'_n = \frac{1}{M-1}\sum_{m=1}^{M-1} (z_m - \bar{z})^2$$

$$u = \begin{pmatrix} \log|u_2| \\ \log|u_3| \\ \log|u'_2| \end{pmatrix}$$

$$v = Tu + t.$$

5. Apparatus according to any preceding claim 1, wherein the preset prior probability distribution is of Dirichlet form or is a mixture of Dirichlets.

6. Apparatus according to claim 5, wherein the preset prior probability distribution is $$P\left(p \mid \sum_i p_i = 1\right) = \frac{\Gamma\left(\sum_i \alpha_i\right)}{\prod_i \Gamma(\alpha_i)} \prod_i p_i^{\alpha_i - 1}$$

where all $\alpha_i > 0$.

7. Apparatus according to claim 1, wherein the marginals are updated using an algorithm carrying out the equation $$\log P(p_i \mid D) = \log P(p_i) + \log(1 - p_i) +$$

$$f\left(\log \frac{p_i}{1 - p_i} - \log \frac{P(E_i)}{1 - P(E_i)} + \log\left(\frac{P(D_{i_1} \mid E_i)P(E_i)}{\sum_{h \neq i} P(D_{i_1} \mid E_h)P(E_h)}\right)\right) + K$$

8. Apparatus according to claim 1, wherein the generating means comprise a means defining a passage through which particles to be measured must pass, means for irradiating the particles, and means for detecting perturbations in the radiation caused by the particles to generate an analog signal.

9. Apparatus according to claim 8 wherein the means for irradiating the particles comprise a source of monochromatic light adapted to produce a structured light field in a measurement volume in said passage, particles in use passing transversely through the structured light field.

10. A method of obtaining a posterior probability distribution $P(p|D)$ relating to an attribute or attributes $\theta$ quantized into I values $(\theta_1, \ldots, \theta_I)$ of a succession of events each one of which is one of the types $(E_1, E_2, \ldots, E_I)$ in which the events generate measurable physical reactions, the posterior probability distribution $P(p|D)$ being on a distribution $P(\theta)$ of $\theta$, where $P(\theta)$ is represented by $p=(p_1, p_2, \ldots p_I)$ where $p_i = P(\theta_i)$; the method comprising:

detecting the physical reactions generated by the events and generating measurements $D=(D_1, D_2, \ldots, D_j, \ldots)$ in response to the detected reactions; and deriving values $P(p_i = q_{i,k}|D)$ at points $q_{i,k}$ of the marginal distributions $P(p_i|D)$ of the probability distribution $P(p|D)$ for the distribution of the attribute or attributes $\theta$ of the events by carrying out a Bayesian inferential process utilising the values $(D_1, D_2, \ldots D_j, \ldots)$, the marginal values $P(p_i = q_{i,k})$ of a preset prior probability distribution $P(p)$ which marginal values define the complete preset prior probability distribution, and a stored set of values $P(D_j|E_i)$ representing a range of probability distributions for the occurrence of each of the observed measurements D from the events of each type of E occurring, the inferential process being an iterative process in which the values $P(p_i = q_{i,k}|D_1, \ldots, D_j)$ of the marginals $P(p_i|D_1, \ldots, D_j)$ after the jth event are generated from the values $P(p_i = q_{i,k}|D_1, \ldots, D_{j-1})$ of the marginals $P(p_i|D_1, \ldots, D_{j-1})$ prior to that event.

11. A method according to claim 10, wherein an analog signal is generated by the events being measured which signal is converted into a digital signal, and the digital signal is compressed prior to the inferential processing.

12. A method according to claim 11, wherein the digital signal is compressed by taking quantized transformed log moments.

13. A method according to claim 10, wherein the preset prior probability distribution is of Dirichlet form or is a mixture of Dirichlets.

* * * * *

UNITED STATES PATENT AND TRADEMARK OFFICE
Certificate

Patent No. 6,381,555 B1            Patented: April 30, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Roger Fane Sewell, Newnham, Great Britain; and Patrick Edward Luffman, Clapham, Great Britain.

Signed and Sealed this Twentieth Day of June 2006.

JOHN E. BARLOW
                               *Supervisory Patent Examiner*
                               Art Unit 2863